United States Patent

Cole et al.

[11] Patent Number: 5,340,567
[45] Date of Patent: Aug. 23, 1994

[54] SUNSCREEN COMPOSITIONS

[75] Inventors: Curtis A. Cole, Langhorne, Pa.; Martin K. O. Lindemann, Bridgewater, N.J.; Elvin R. Lukenbach, Flemington, N.J.; Ralph C. Stutzman, Ringoes, N.J.

[73] Assignee: Johnson & Johnson Consumer Products, Inc., Skillman, N.J.

[21] Appl. No.: 827,908

[22] Filed: Jan. 30, 1992

Related U.S. Application Data

[63] Continuation of Ser. No. 452,028, Dec. 15, 1989, abandoned.

[51] Int. Cl.⁵ ............................ A61K 7/42; A61K 9/10
[52] U.S. Cl. .......................................... 424/59; 514/938
[58] Field of Search ............................................ 424/59

[56] References Cited

U.S. PATENT DOCUMENTS

| | | | |
|---|---|---|---|
| 2,826,169 | 3/1958 | Le Veen | 424/59 X |
| 4,671,955 | 6/1987 | Palinczar | 424/59 |
| 4,927,464 | 5/1990 | Cowie | 424/59 |
| 5,028,417 | 7/1992 | Bhat et al. | 424/59 |

FOREIGN PATENT DOCUMENTS

| | | | |
|---|---|---|---|
| 2533497 | 2/1977 | Fed. Rep. of Germany | 424/59 |
| 3642794A1 | 6/1987 | Fed. Rep. of Germany | 424/59 |
| 3836630 | 5/1989 | Fed. Rep. of Germany | 424/59 |
| 0062106 | 4/1983 | Japan | 424/59 |
| 2211736A | 2/1986 | Japan | 424/59 |
| 1078715 | 4/1986 | Japan | 424/59 |
| 2184356 | 6/1987 | United Kingdom | 424/59 |
| 2111409A | 7/1989 | United Kingdom | 424/59 |

OTHER PUBLICATIONS

Bennett, The Cosmetic Formula, 1937, pp. 79 to 81, 229 & 230.
Chem. Abs., 1986, vol. 105, 102509f, Matsueda et al.
Patent Abstract of Japan 60-231607 (1985), vol. 10, No. 98, p. 164C 339.

*Primary Examiner*—Dale R. Ore

[57] ABSTRACT

Novel sunscreen compositions containing titanium dioxide having a particle size less than about 35 m$\mu$ and zinc oxide having a particle size less than about 50 m$\mu$ are described as well as methods of protecting the skin from damaging ultraviolet radiation.

8 Claims, No Drawings

SUNSCREEN COMPOSITIONS

This is a continuation of application Ser. No. 07/452,028, filed Dec. 15, 1989 now abandoned.

BACKGROUND OF THE INVENTION

This invention relates to new and useful ultraviolet radiation sunscreen agents and compositions and to methods of protecting human skin against the potentially harmful effects of sunlight.

Although a tan has long been considered a status symbol indicative of good health and the ability to secure sufficient leisure time to enjoy outdoor activities such as swimming, tennis, golf, skiing and the like, it has become very evident that excessive exposure of the human skin to sunlight is harmful.

It is well documented that human skin is sensitive to sunlight and artificial light containing radiation of wavelengths between about 290 nanometers (nm) and 400 nm. Ultraviolet radiation of wavelengths between about 290 nm and 320 nm (UV-B region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years, concern has also been expressed regarding ultraviolet radiation of wavelengths above 320 nm (UV-A region) and the adverse effects of such radiation on human skin. The radiation between 320 and 400 nm also contributes to the premature aging of the skin. In addition, recent studies indicate that chronic sun exposure limits the immuno-response of the skin. There is also evidence that a tan will offer some protection against burning but is quite ineffectual against other types of solar damage.

Growing public awareness that the enjoyment of outdoor activities must go hand in hand with adequate sun protection has led to an unprecedented growth in the area of sunscreen products. A desirable sunscreen product should have the following attributes: protection in both the UV-A and UV-B ultraviolet radiation ranges; maintenance of coverage, i.e., waterproof and perspiration proof; application and use convenience, i.e., ease of application, invisibility, non-staining and non-greasy; and freedom from irritation as a result of its ingredients, in particular, its active sunscreen ingredients. Of recent interest in this area have been some concerns over the irritancy and sensitization problems that may occur in some individuals utilizing sunscreen products with high SPF values containing organic sunscreen agents.

The effectiveness of a sunscreen product is indicated by its sun protection factor (SPF). The sun protection factor is the ratio of the amount of exposure (dose) required to produce a minimal erythema reaction in protected skin to the amount required to produce the same reaction in unprotected skin. The absolute dose differs from person to person and is largely dependent on one's genetic predisposition and ethnic origin. If a person would normally require ten minute exposure to sunlight to develop a minimal erythema reaction, this person when using an SPF 15 sunscreen product should be able to tolerate up to 150 minutes of sunlight without an erythema reaction. Recent public awareness of the problems of exposure to sunlight has led to a demand for sunscreen products with high SPF values, i.e., at or above SPF 8.

Ease of application and cosmetic appeal, on the other hand, rely on subjective evaluations such as visual and tactile impression by the user. Consumer research studies indicate that a sunscreen formulation should rub in easily, leave the skin non-sticky and, above all, should be invisible on the skin after application.

OBJECTS OF THE INVENTION

It is an object of the present invention to provide improved sunscreen agents and compositions.

It is another object of the present invention to provide sunscreen compositions containing sunscreen agents that overcome the disadvantages of heretofore available materials and provide adequate and safe protection for human skin.

It is a further object of this invention to provide methods of protecting human skin against the harmful effects of sunlight.

These and other objects and features of the present invention will become readily apparent to one skilled in the art from the detailed description given hereinafter.

SUMMARY OF THE INVENTION

The foregoing objects and other features and advantages of the present invention are achieved by sunscreen compositions containing inorganic sunscreen agents as the active ingredients. More particularly, the present invention relates to sunscreen compositions containing titanium dioxide and zinc oxide of specific particle size ranges and in specific amounts and ratios as the sunscreen agents. These specific compositions permit the use of lower amounts of the sunscreen active ingredients while still achieving the desired high SPF values for the compositions.

The prior art contains a number of disclosures showing the use of titanium dioxide and zinc oxide as sunscreen materials, in various formulations including the following.

In Japanese Patent Application No. 1981 - 161,881, there is a disclosure of cosmetics containing 0.1–40% of ultrafinely divided titanium oxide with a particle size of 10–30 m$\mu$ which has been rendered hydrophobic. It is indicated that when hydrophobically treated titanium oxide with a particle size of 10–30 m$\mu$ is blended into cosmetic base materials, it transmits visible light but reflects and scatters the harmful ultraviolet rays. Unfortunately, it has been found that when titanium dioxide of this particle size range is utilized as a sunscreen agent in sunscreen compositions, it may result in the loss of one of the most desired properties of such compositions, i.e., invisibility. Products containing titanium dioxide of the particle size disclosed in this application usually have a white color or cast to them and, therefore, are not invisible. In order to overcome the lack of invisibility or whiteness, specific processing techniques are required.

In a co-pending application Ser. No. 75,713, filed Jul. 20, 1987, sunscreen compositions containing microfine titanium dioxide are disclosed. The particle size of the titanium dioxide is required to be less than 10 m$\mu$. It is also indicated that other sunscreen agents can be utilized with the titanium dioxide.

In German Patent No. 3,642,794 (1987) there is disclosed a cosmetic composition for preventing sunburn which contains 1–25 % zinc oxide of a particle size of 70–300 microns, and it is further indicated that the composition may also contain titanium dioxide of a particle size of 30–70 microns. This composition would not be desirable because of its unaesthetic whiteness characteristics at high SPF levels.

In Japanese Patent No. 60,231,607 (1985) there is disclosed a sunscreen cosmetic containing 1–30% zinc oxide powder of particle size from 10–60 m$\mu$. No other sunscreen agents are disclosed.

In Japanese Patent No. 72,042,502 there is disclosed an antisunburn cosmetic containing titanium dioxide having a particle size of 30–40 m$\mu$ and it is indicated that a synergistic effect may be achieved by using titanium dioxide with other known UV absorbents but none are disclosed in the abstract.

DETAILED DESCRIPTION OF THE INVENTION

The sunscreen compositions of the present invention contain as active sunscreen agents, microfine titanium dioxide of a specific particle size, i.e., less than about 35 millimicrons (hereinafter designated as "m$\mu$") and microfine zinc oxide of a specific particle size, i.e., less than about 50 m$\mu$.

The use of the specific titanium dioxide in the above compositions have been found to enhance solar radiation protection without detracting from desirable cosmetic properties such as ease of application and, most importantly, invisibility.

Titanium dioxide is an inorganic substance which is widely used as a pigment in oil and latex paints where a pure white color is desired. It is also employed as an additive in cosmetic products such as bar soaps to enhance the whiteness and opacity of the product. This property of titanium dioxide results from its ability to scatter visible radiation. To obtain maximal scattering and hence whiteness, the particle size of commonly used titanium dioxide is generally between 150 and 350 m$\mu$. Titanium dioxide also absorbs and scatters UV-radiation. As is the case with visible light, optimal scattering is a function of the particle size while absorption of UV-radiation is an inherent property of the titanium dioxide molecule itself.

It is highly desirable that a sunscreen composition after application to the skin should be invisible. Since the scattering of visible light results in an ungainly whitish appearance of the skin, it is essential that the particle size and the processing to prepare the selected titanium dioxide as well as the resulting compositions in which it is utilized maximize UV-B and UV-A absorption and minimize scattering of visible light.

As stated above, the microfine titanium dioxide useful in the present invention is of a particle size of less than about 35 m$\mu$, preferably less than about 10 m$\mu$. The titanium dioxide useful in the present invention can be prepared by well-known commercial methods. One such method is the classic sulfate process discussed in the Kirk-Othmer Encyclopedia, Vol. 23, on page 143 and set forth in a flow diagram on page 146. The essential step in this process is hydrolysis, under carefully controlled conditions, of an acid solution of titanyl sulfate yielding a hydrous precipitate. This precipitate contains adsorbed sulfuric acid (pH ~ 1) and the resulting pigments are unsuitable for cosmetic applications. To render it suitable for such uses, it is neutralized with barium hydroxide to obtain a pH of about 3 to 6 and calcinated to increase the particle size. As a result of this process, the resulting titanium dioxide is usually present in a mixture with barium sulfate. Other processes are available which do not utilize barium hydroxide as a neutralizing agent. If desired, for stability purposes, these particles can be coated with stearic acid or other suitable materials.

The titanium dioxide useful in the present invention should be present in an amount of from about 2.0 to 25.0% by weight of the total composition, preferably from about 2.0 to 15.0%.

The other sunscreen agent useful in the compositions of the present invention is zinc oxide of a specific particle size. Zinc oxide is an inorganic substance which, conventionally serves as a white pigment in paints, papers, and polymers among other uses. It also has been utilized as a physical sunblock in personal care products. It functions as a pigment by scattering the visible light due to its high index of refraction compared with vehicle components and also due to its particle size range of 200–350 m$\mu$. Zinc oxide also scatters and absorbs ultraviolet radiation. The scattering of visible and ultraviolet radiation is a function of particle size, while absorption of UV radiation is an inherent property of the zinc oxide itself.

It is highly desirable that a sunscreen composition after application to the skin should be invisible. Since the scattering of visible light results in an ungainly whitish appearance of the skin, it is essential that the particle size and the processing to prepare the selected zinc oxide as well as the resulting compositions in which it is utilized maximize UVB and UVA absorption and minimize scattering of visible light.

It has been found that when the zinc oxide of the compositions of the present invention, i.e., particle size less than about 50 m$\mu$, preferably less than about 20 m$\mu$, is utilized, such compositions upon use on the skin are invisible and, therefore, highly desirable.

The zinc oxide useful in the present invention can be prepared by a number of methods well known in the chemistry of zinc. The essential step in such processes is the precipitation under carefully controlled conditions, of an insoluble microfine zinc salt prepared from soluble forms of the zinc ion and precipitating anion. The thus formed insoluble salt must be of such nature that it may be subsequently converted to zinc oxide in a solid state reaction, for example by heat treatment. Specifically, an aqueous solution of zinc sulfate combined with aqueous sodium carbonate results in the precipitation of microfine zinc carbonate, which may be pyrolyzed to zinc oxide by driving off carbon dioxide thereby yielding small particle size zinc oxide.

The zinc oxide useful in the present invention should be present in an amount of from about 2.0 to 25.0% by weight of the total composition, preferably from about 2.0 to 15.0%.

The total amount of the titanium dioxide and zinc oxide by weight of the total composition should be from about 4.0 to 25.0%. If less than about 4.0% by weight of the total composition is utilized, then one will not achieve the desired high SPF values and if greater than 25.0% by weight of the total composition is utilized, processing and economic factors come into consideration.

In connection with the sunscreen compositions of the present invention, it has further been found that when the titanium dioxide and zinc oxide are in a weight ratio of from about 1:25 to 10:1, preferably 1:8 to 3:1, they act as a synergistic combination with respect to SPF values.

The term "synergistic combination" as used herein refers to a combination of sunscreen actives, i.e., titanium dioxide of a particular particle size and zinc oxide of a particular particle size which, at a given total concentration, yield higher SPF values than either of the two ingredients individually at the same total concentration. This is such because the SPF values are related to absorbancy of UV light in a non-linear fashion and therefore, synergism cannot be expressed by the mere addition of the SPF values of the two ingredients per se. Alternatively, sunscreen combinations using a lower total concentration exhibiting SPF values equal to or greater than the SPF values of either of the individual sunscreen agents alone also demonstrate synergy.

The sunscreen compositions of the present invention contain titanium dioxide and zinc oxide as the sunscreen agents and an extending medium such as a carrier or vehicle which adapts said agents for application to the skin. Included in these vehicles or carriers can be materials selected from a class known as "filler" materials. It has been observed that when certain of these materials are present, such as clays and talc, the SPF values of the resulting compositions are somewhat enhanced even though these materials when utilized in compositions without sunscreen actives exhibit negligible SPF values. The compositions of the present invention can be in either solid, liquid or aerosol form. The sunscreen agents of the present invention can also be incorporated into various cosmetic and personal care products such as hand and body lotions, oils, ointments, lip balm products, facial cosmetics and the like.

Specific embodiments of the present invention are illustrated by the following examples. It will be understood, however, that the invention is not confined to the specific limitations set forth in the individual examples, but rather to the scope of the appended claims.

EXAMPLE I

An anhydrous sunscreen ointment composition is prepared as follows:

50.0 g. of mineral oil and 5.0 g of powdered polyethylene are mixed with 35.0 g. of a dispersion of 70 parts titanium dioxide (particle size < 10 m$\mu$) in 30 parts isostearic acid at a temperature of about 95° C. until a homogeneous melt is obtained. With constant stirring 10.0 g. of microfine zinc oxide (particle size of 18 m$\mu$) are added and uniformly dispersed. Stirring is continued while the mixture is allowed to cool down to ambient temperature.

The resulting composition has the following formulation:

| Ingredient | % w/w |
|---|---|
| mineral oil | 50.0 |
| polyethylene | 5.0 |
| zinc oxide | 10.0 |
| titanium dioxide | 24.5 |
| isostearic acid | 10.5 |
| | 100.0 |

The in-vitro SPF (Sun Protection Factor) of this composition is measured using the system described by Cole and VanFossen [Cole, C., VanFossen R., (1990) In-vitro model for UVB and UVA protection. In: *Sunscreens: Development, Evaluation and Regulatory Aspects*, N. Shaath and N. Lowe Eds., Marcel Dekker Pub. New York, N.Y. (in press)]. Briefly, this system consists of the measurement of transmission of solar simulated UV radiation through composition (1.2 mg/cm$^2$) applied to the skin. The excised mouse skin with and without a sunscreen measurement system consists of an optical sensor that is only sensitive to sunburning radiation and has a sensitivity spectrum similar to the human erythema sensitivity spectrum. The SPF is the ratio of the optical signal through the skin (no sunscreen) divided by the optical signal through the skin with the sunscreen. The system is calibrated against a series of sunscreens of known SPF (4 through 36) determined in-vivo using the FDA monograph method (Federal Register, Aug. 25, 1978, Sunscreen drug products for over-the-counter human drugs. pp 38206–38269.) The resulting SPF of the composition of Example I above is 32 and the composition is aesthetically satisfactory.

EXAMPLE II

An anhydrous sunscreen ointment composition is prepared according to the procedure of Example I by admixing 58.4 g. of mineral oil with 20.8g of a predispersion of 60 parts titanium dioxide (particle size < 10 m$\mu$) and 40 parts isostearic acid, 12.5 g. zinc oxide (particle size 18 m$\mu$) and 8.3 g. isostearic acid. The resulting composition has the following formulation:

| Ingredient | % of w/w |
|---|---|
| mineral oil | 58.4 |
| zinc oxide | 12.5 |
| titanium dioxide | 12.5 |
| isostearic acid | 16.6 |
| | 100.0 |

When this composition is tested according to the in-vitro test procedure of Example I, the SPF is 24. The resulting composition is aesthetically satisfactory.

When the zinc oxide in the above formulation is removed and replaced by an equal weight amount of titanium dioxide (total TiO$_2$ = 25.0%) the resulting SPF is 14 and when the titanium dioxide is removed and replaced by an equal weight amount of zinc oxide (total ZnO = 25.0%) the resulting SPF is 17. The differences in the SPF values are significant and this demonstrates the synergism of the combination of titanium dioxide and zinc oxide in the compositions of the present invention.

EXAMPLE III

A sunscreen lotion composition is prepared as follows:

380.35 g. of deionized water, 18.75 g. of an acrylic/acrylate copolymer (Carboset) and 5.0 g. of a 7.5% (w/v) ammonium hydroxide solution are admixed and stirred vigorously at room temperature until complete dissolution is achieved.

In a separate container, 5.0 g. of polyethylene and 50.0 g. of mineral oil are heated with mixing to 95° C. or until the polyethylene is melted. To this mixture is added 30.0 g. of sorbitan sesquioleate, 30.0 g. of PEG-7 castor wax, 22.5 g. of hydroxylated lanolin, and 130.0 g. of a dispersion of hectorite clay in isopropyl myristate. The mixture is stirred while maintaining a temperature of 60° C.–65° C. until a uniform melt is achieved. To this mixture is added 90.9 g. of a dispersion of 33% TiO$_2$ (particle size 20 m$\mu$) in a mixture of mineral oil and triglycerides followed by the slow addition of 107.5 g. of microfine zinc oxide (particle size 18 m$\mu$). After the uniform incorporation of the particulate matter, the temperature is adjusted to 55° C. and 50.0 g. of cyclomethicone (Silicone Fluid 344-Dow Corning) and 80.0 g. of cyclomethicone (Silicone Fluid 345-Dow Corning) are added. At this point the previously prepared water phase is combined with this mixture under strong agitation. Stirring is continued and the emulsion is allowed to cool slowly.

The resulting composition has the following formulation:

| Ingredient | % of w/w |
| --- | --- |
| polyethylene | 0.50 |
| mineral oil | 5.00 |
| Silicone Fluid #344 | 5.00 |
| Silicone Fluid #345 | 8.00 |
| hectorite clay/isopropyl myristate dispersion | 13.00 |
| sorbitan sesquioleate | 3.00 |
| PEG-7 castor oil | 3.00 |
| hydroxylated lanolin | 2.250 |
| titanium dioxide | 3.000 |
| zinc oxide | 10.750 |
| mineral oil/triglycerides mixture | 6.090 |
| acrylic/acrylate copolymer | 1.875 |
| ammonium hydroxide (7½% soln.) | 0.500 |
| water | 38.035 |
| | 100.000 |

The finished product has a viscosity of about 13,000 cps and an SPF of 25.

This product is subjected to a whiteness test as follows:

0.5 ml of the productis spread over a 3 in. square of black art-construction paper and allowed to "dry" for 1 to 2 hours. Ten whiteness measurements are taken (using a Minolta Chroma Meter) on the L*a*b* color system scale. These measurements are taken in a uniform pattern over the total surface area.

The whiteness value (L*) is an average of the ten values. This L* value correlates well with human observations of product utilized on skin for transparency. The L* values represent shades between 0=black to 100=white with values greater than 50 being deemed aesthetically unacceptable.

When the product of Example III is tested for whiteness according to the above procedure it has an L* value of 37.5 which is very satisfactory.

EXAMPLE IV

A sunscreen cream composition is prepared as follows:

20.0 g. of polysodium methacrylate (Alcosperse 125) is mixed in 499.5 g. of deionized water and then 27.0 g. of propylene glycol, 1.5 g. methylparaben, 1.0 g. of disodium EDTA and 7.00 g. magnesium sulfate are added. The mixture is then heated to 80° C. and 30.0 g. of microfine titanium dioxide (particle size<10 mµ) are dispersed therein with agitation.

In a separate container, 168.0 g. of mineral oil, 10.0 g. of magnesium stearate, 60.0 g. of a mixture of sorbitan oleate, castor wax, beeswax and stearic acid (Arlacel 481), 20.0 g. of PEG-7 castor wax and 50.0 g. of isopropyl myristate are added under constant stirring. The mixture is heated to 80°-85° C. and when a uniform melt is obtained, 100.0 g. of microfine zinc oxide (particle size 18 mµ) are slowly stirred into the mixture.

The oil phase is added to the water phase with vigorous stirring and cooled slowly while continuing to mix. At a temperature of 40° C., 6.0 g. of a 33% solution of Quaternium 15 (Dowicil 200) are added and the mixture is homogenized while warm.

The resulting composition has the following formulation:

| Ingredient | % of w/w |
| --- | --- |
| mineral oil | 16.80 |
| magnesium stearate | 1.00 |
| Arlacel 481 | 6.00 |
| PEG-7 castor oil | 2.00 |
| isopropyl myristate | 5.00 |
| zinc oxide | 10.00 |
| titanium dioxide | 3.00 |
| propylene glycol | 2.70 |
| methylparaben | 0.15 |
| disodium EDTA | 0.10 |
| magnesium sulfate | 0.70 |
| Dowicil 200 (33%) | 0.60 |
| Alcosperse 125 | 2.00 |
| deionized water | 49.95 |
| | 100.00 |

The final product has a viscosity of 108000 cps, an SPF value of 16 and a L* value of 40.

In addition to the preferred embodiments described herein, other embodiments, arrangements and variations within the spirit of the invention and the scope of the appended claims will occur to those skilled in the art.

What is claimed is:

1. A sunscreen composition comprising an extending medium and a synergistic combination of titanium dioxide having a particle size of less than about 35 mµ and zinc oxide having a particle size of less than about 50 mµ; said titanium dioxide and zinc oxide being present in a weight ratio of from about 1:25 to 10:1 and the total of said titanium dioxide and zinc oxide comprising from about 4.0 to about 25.0% by weight of the total composition.

2. The sunscreen composition of claim 1 where the particle size of the titanium dioxide is less than about 10 mµ.

3. The sunscreen composition of claim 1 wherein the particle size of the zinc oxide is about 18 mµ.

4. The sunscreen composition of claim 1 containing from about 2.0 to 15.0% by weight of the total composition of titanium dioxide.

5. The sunscreen composition of claim 1 containing from about 2.0 to 15.0% by weight of the total composition of zinc oxide.

6. The sunscreen composition of claim 1 wherein the titanium dioxide and zinc oxide are present in a weight ratio of from about 1:8 to 3:1.

7. A method of protecting human skin from the erythremic effects of ultraviolet radiation which comprises applying to the skin a sunscreen composition containing an extending medium and a synergistic combination of titanium dioxide having a particle size of less than about 35 mµ and zinc oxide having a particle size of less than about 50 mµ; said titanium dioxide and zinc oxide being present in a weight ratio of from about 1:25 to 10:1 and the total of said titanium dioxide and zinc oxide comprising from about 4.0 to about 25.0% by weight of the total composition.

8. The method of claim 7 wherein the titanium dioxide and zinc oxide are present in a weight ratio of from about 1:8 to 3:1.

* * * * *